United States Patent [19]
Reed

[11] Patent Number: 5,172,586
[45] Date of Patent: Dec. 22, 1992

[54] SYSTEM AND METHOD FOR DETERMINING VAPOR PRESSURE OF LIQUID COMPOSITIONS

[75] Inventor: Donald B. Reed, Plano, Tex.

[73] Assignee: Atlantic Richfield Company, Los Angeles, Calif.

[21] Appl. No.: 604,717

[22] Filed: Oct. 26, 1990

[51] Int. Cl.$^5$ .............................................. G01N 7/14
[52] U.S. Cl. .................................................. 73/64.45
[58] Field of Search ................... 73/64.2, 19.01, 19.05, 73/53, 61.3

[56] References Cited

U.S. PATENT DOCUMENTS

| | | | |
|---|---|---|---|
| 3,528,440 | 9/1970 | Plucker | 73/64.2 |
| 4,543,819 | 10/1985 | Chin et al. | 73/64.2 |
| 4,783,989 | 11/1988 | Reed | 73/64.2 |
| 4,905,505 | 3/1990 | Reed | 73/64.2 |

Primary Examiner—Hezron E. Williams
Assistant Examiner—Michael J. Brock
Attorney, Agent, or Firm—Michael E. Martin

[57] ABSTRACT

True vapor pressure of liquid compositions, particularly multi-component compositions, is measured by a piston and cylinder apparatus defining an expansible chamber in which a simple of liquid is trapped, the chamber is expanded in multiple steps and multiple pressure and temperature measurements are taken at each expansion over a period of time. A resultant pressure at each expansion is determined from multiple measurements using the least squares method of approximation and the plural resultant pressure values are extrapolated to determine true vapor pressure using a straight-line approximation. The apparatus is adapted to continuously measure vapor pressure of a process stream by sampling a slipstream of liquid which is maintained at a constant temperature. The apparatus cylinder includes a bore which is closed at one end by a pressure transducer defining an end wall of the measurement chamber. The apparatus is mounted horizontally to minimize liquid depth and increase the rate of bubble formation during expansion of the chamber.

18 Claims, 3 Drawing Sheets

SYSTEM AND METHOD FOR DETERMINING VAPOR PRESSURE OF LIQUID COMPOSITIONS

BACKGROUND OF THE INVENTION

1. Field of the Invention

The present invention pertains to a cylinder and piston type device for making measurements of vapor pressure of liquid compositions, together with a method of making such measurements of true vapor pressure of a multi-component liquid composition, in particular.

2. Background

U.S. Pat. No. 4,783,989, assigned to the assignee of the present invention, describes a vapor pressure measurement system having a cylinder member in which a reciprocable piston is disposed for movement to contain a sample of liquid and to expand a chamber formed by the cylinder and piston while measuring the pressure in the chamber until a pressure is obtained indicative of the vapor pressure of the liquid. In the further development of a system along the lines of that described in the abovementioned patent, it has been determined that improvements in the fluid inlet and outlet flow paths and valving was required and that the relationship of the surface area of liquid to the depth of liquid in the chamber should be increased to reduce the liquid path length through which vapor bubbles are required to travel in order for an equilibrium condition of vapor and liquid to be reached in a reasonable period of time. This is particularly important for multi-component liquids such as crude oil and refined petroleum liquids.

Still further, in order to improve the accuracy of measurement of vapor pressure in a device generally of the type described in the above-referenced patent, and to reduce the time required to take measurements, it has been determined that an improved methodology was necessary. Briefly, at least two measurement points were deemed necessary to establish an accurate estimation of the true vapor pressure, and the time required to make the measurements should be reduced so that the apparatus can be used on a continuous basis to make measurements of process and transport flowstreams. It is to these ends that the present invention was developed with a view to providing an improved vapor pressure analyzer and method of estimating true vapor pressure of various liquids, particularly multi-component liquids such as crude oil and refined petroleum products.

SUMMARY OF THE INVENTION

The present invention provides an improved apparatus for making vapor pressure measurements of various liquid compositions wherein the time required to establish equilibrium conditions in a piston and cylinder type apparatus is minimized. In accordance with one important aspect of the present invention, a vapor pressure analyzing apparatus is provided with a piston disposed in a cylinder for expansion of a chamber in incremental stages and wherein the cylinder is arranged with its longitudinal central axis substantially horizontal to minimize the depth of liquid in the chamber during the various phases of the measurement process.

Still further in accordance with the present invention, an improved system for making vapor pressure measurements is provided wherein temperature control of the fluid during the testing process is more easily accomplished, the chance of leakage of volatile fluids from the apparatus into the environment is minimized and a system is provided which is relatively uncomplicated yet is well suited to making vapor pressure measurements of various kinds of liquids and allows calibration of the system with relative ease.

In accordance with yet another important aspect of the present invention, an improved method of making vapor pressure measurements with an expansible chamber-type vapor pressure analyzer is provided wherein accurate estimates of true vapor pressure are made without prolonged measurement time. An asymptotic pressure value is calculated for at least two conditions of relationship of vapor space to liquid space in an expansible chamber apparatus, and an extrapolation is made for a relationship wherein the vapor space to the liquid space equals zero to provide a value of vapor pressure at the onset of expansion of the chamber, preferably using a straight-line approximation. Such an approach for certain types of fluids tested indicates that the calculated vapor pressure only very slightly underestimates the actual true vapor pressure, the actual degree of underestimation being dependent on the type of fluid being measured.

Those skilled in the art will recognize the abovedescribed features and advantages of the present invention, as well as other superior aspects thereof upon reading the detailed description which follows in conjunction with the drawings.

DESCRIPTION OF PREFERRED EMBODIMENTS

In the description which follows, like parts are marked throughout the specification and drawing with the same reference numerals, respectively. The drawing figures are not necessarily to scale, and some elements may be shown in schematic form in the interest of clarity and conciseness. The subject matter of U.S. Pat. No. 4,783,989, issued Nov. 15, 1988, is incorporated herein by reference.

Figure 1:
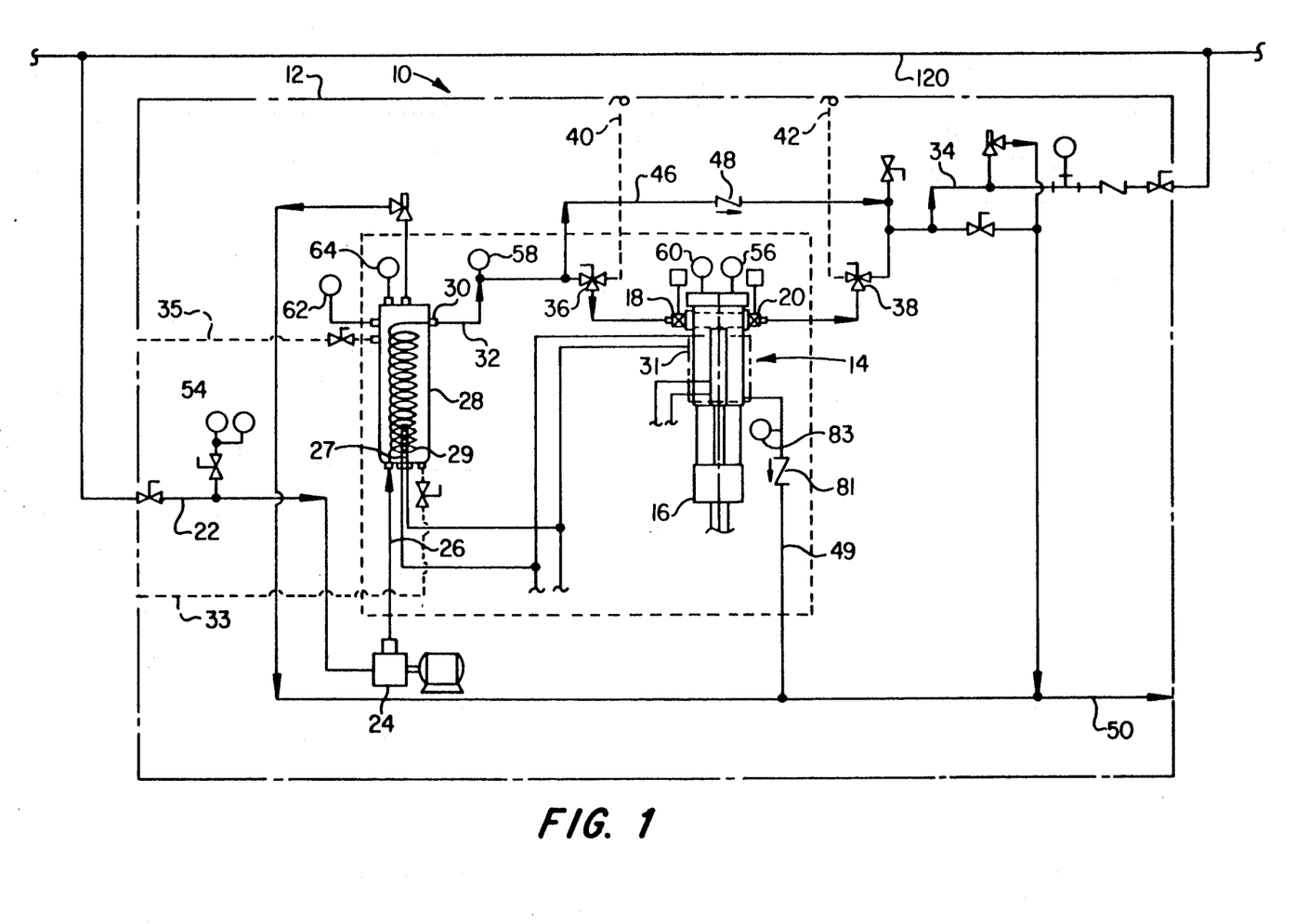
FIG. 1 is a schematic diagram of an improved vapor pressure measurement system in accordance with the present invention.

Referring to FIG. 1, there is shown a schematic diagram of a system in accordance with the present invention, which is generally designated by the numeral 10. The system 10 is adapted to be disposed on or within an enclosure 12 and includes a piston and cylinder apparatus 14, which is actuated by a linear controllable electric actuator 16 of a type described in the referenced patent. The actuator 16 is operable to move a piston within a cylinder of the apparatus 14, to be described in further detail herein, to carry out certain pressure measurements within the cylinder of a quantity of fluid trapped within the cylinder between opposed inlet and discharge valves 18 and 20, respectively. A fluid slipstream to be sampled and tested is conducted to the system 10 for entry into an inlet conduit 22 and is circulated through the system by a motordriven pump 24. A discharge conduit 26 of the pump 24 is connected to a shell and tube type heat exchanger 28. A continuous tube coil 29 is disposed in the heat exchanger 28 for conducting fluid to be sampled therethrough. The heat exchanger 28 has a discharge port 30 which is connected to a conduit 32 which leads to the inlet valve 18. The fluid slipstream leaving the apparatus 14 by way of the discharge valve 20 is conducted back to the source of fluid by way of a conduit 34 or to other suitable means for disposing of the fluid. Suitable valves 36 and 38 are interposed in the conduits 32 and 34 and are connected to respective conduits 40 and 42 to provide for isolating the apparatus 14 from the conduits 32 and 34 so that a calibration fluid stream may be circulated through the apparatus for calibration measurements, as needed. A bypass conduit 46 is connected across the conduits 32 and 34 and is provided with a suitable check valve 48 whereby fluid may be continually circulated through the system 10 while measurements are being conducted and the valves 18 and/or 20 are closed. Suitable vent and drain lines are shown schematically in FIG. 1 but will be omitted from this discussion in the interest of clarity and conciseness, save reference to a drain line 49 connected to the apparatus 14 for a purpose which will be discussed in further detail herein. The drain line 49 is connected to a conduit 50 which leads to suitable means, not shown, for draining working fluid from the system 10.

Figure 2:
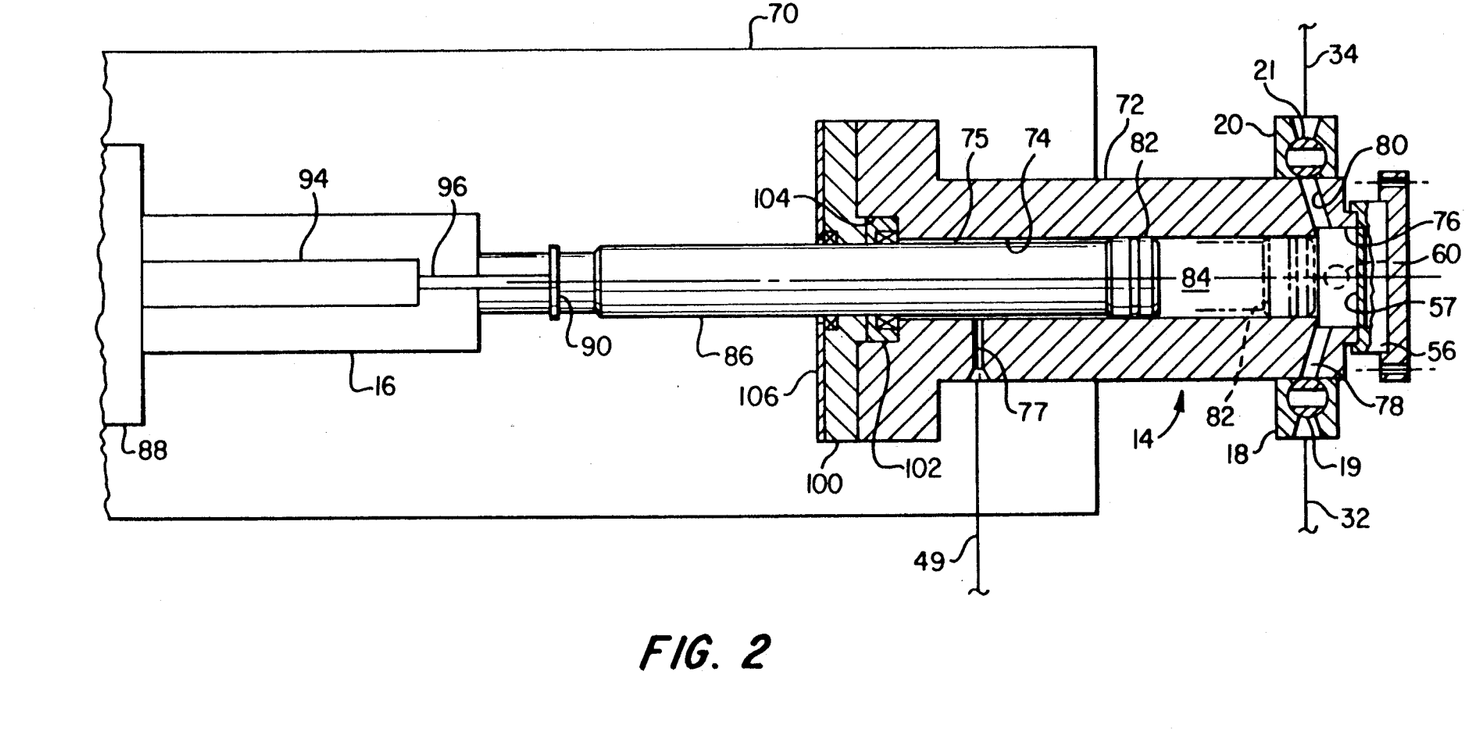
FIG. 2 is a central section view of the expansible chamber measurement apparatus according to the present invention.

The heat exchanger 28 may be adapted to maintain the temperature of the liquid being tested at a constant value and may require heating of the liquid or cooling of the liquid. Heating of the liquid may be carried out by way of a heating element 27 disposed within the apparatus 28 for heating a heat exchange fluid disposed within the apparatus. Alternatively, a heat exchange fluid may be circulated through the heat exchanger 28 by way of conduits 33 and 35 to achieve the desired temperature of the test fluid leaving the heat exchanger by way of the conduit 32. The apparatus 14 may also be temperature controlled by an electrically energized heating blanket or wrap 31. Liquid pressure measurements are preferably taken at pressure sensors 54 and 56. Temperature sensors 58 and 60 may be used to control the operation of the heating element 27 and wrap 31. The sensor 60 is preferably disposed to sense the temperature of the fluid to be sampled in the apparatus measurement chamber as shown in FIG. 2. It may be desirable to also know the pressure and temperature of the heat exchange fluid being circulated through the heat exchanger 28, which pressure and temperature may be sensed and recorded by suitable sensors 62 and 64, respectively.

Control functions for the system 10 may be carried out utilizing the devices described in U.S. Pat. No. 4,783,989. Suffice it to say that those of ordinary skill in the art may be capable of assembling the system 10 and providing suitable pressure and temperature sensing means, as well as controlling the operation of the pump 24 and the actuator 16 based on the description of the invention herein.

Referring now to FIG. 2, the apparatus 14 is preferably supported on a bracket 70, together with the actuator 16, in a suitable manner. The apparatus 14 includes an elongated cylinder member 72, having a central cylindrical bore 74 formed therein and which has an enlarged portion 76 at one end into which fluid inlet and discharge passages 78 and 80 penetrate. As illustrated in FIG. 2, which is partially a schematic plan view with a longitudinal central section taken of the cylinder 72, the fluid inlet and discharge valves 18 and 20 are configured as ball-type valves having ball closure members 19 and 21, respectively, and which are configured to minimize trapping of vapor bubbles in the passages 78 and 80. The apparatus 14 further includes a piston 82 disposed in the bore 74 for reciprocating movement therein to change the volume of a chamber 84 comprising the measurement chamber for determining the vapor pressure of a liquid composition. The piston 82 includes an elongated rod portion 86 which is suitably connected to the actuator 16. The actuator 16 is preferably a linear type, such as made by Industrial Devices, Inc., Novato, Calif. Moreover, the valves 18 and 20 are preferably a ball-type valve manufactured by Whitey Corporation of Highland Heights, Ohio. The actuator 16 is operably connected to a motor 88 of a suitable type for operating the actuator. The rod 86 is connected to a bracket 90 which is, in turn, connected to a displacement transducer 94 which includes a rod member 96 suitably connected to the bracket 90. The transducer 94 is of a linear variable differential transformer type manufactured by MTS Corporation of Research Triangle Park, N.C.. and is operable to sense the position of the piston 82 with respect to the cylinder 72 and, thus, enables determination of the volume of the chamber 84 at selected positions of the piston 82.

As illustrated in FIG. 2, the piston rod 86 is of a diameter slightly less than the piston 82 to provide an annular passageway 75 between the rod 86 and the cylinder bore 74 through which any leakage fluid may flow to a passage 77 for discharge through the conduit 49. As shown in FIG. 1, the conduit 49 is provided with a spring biased check or minimum pressure valve 81 interposed therein and a pressure sensor 83. If leakage flow from the passage 77 is excessive, the sensor 83 is operably connected to the apparatus control system in such a way as to shut down the system or at least provide a fault signal. The cylinder 72 is closed at the end opposite the chamber portion 76 by a cover plate 100 which is adapted to retain a seal assembly 102 in a stepped-bore portion 104 formed in the cylinder 72. A secondary seal 106 is also engagable with the piston rod 86 to minimize the chance of leakage of volatile or hazardous liquids from the cylinder apparatus 14.

A unique arrangement of the apparatus 14 is provided by the disposition of a pressure transducer 56 forming a head portion of the cylinder 72 and closing one end of the bore portion 76 and the chamber 84. The pressure transducer 56 is preferably a model Series 1151 manufactured by Rosemount, Inc. of Edin Prairie, Minn.

Several aspects of the apparatus 14 are provided to minimize errors in determining the vapor pressure of a liquid composition. In order to minimize leakage of the liquid sample, the diameter of the piston 82 with respect to the length of stroke of the piston is determined to be, preferably, less than 1.0. The smaller diameter of the piston 82 minimizes the leakage of liquid from the chamber 84 past a conventional piston seal ring to the passage 75 and, of course, leakage of liquid or gas in the opposite direction. Still further, more accurate control over the change in volume of the chamber 84 can be provided using a sensing and control device such as the displacement transducer 94. The longitudinal central axis of the bore 74 is, preferably, substantially horizontal. This arrangement, in combination with the piston diameter to stroke ratio, maximizes the surface area of liquid in the chamber 84 as the piston 82 is moved from a minimum volume position to a maximum volume position of the chamber 84, and a shallow depth of liquid under these conditions assures that vapor bubbles forming in the liquid will rapidly move out of the liquid into the vapor space of the chamber as the piston 82 is stroked from its minimum volume position toward its maximum volume position.

The arrangement of the passages 78 and 80 is such that, as liquid is conducted through the chamber 84 from the inlet valve 18 to the discharge valve 20, there is minimal space for the trapping or accumulation of vapor bubbles. In this way, the passages 78 and 80 are either arranged to enter the lower and upper regions of the bore 76, respectively, or, alternatively, the cylinder 72 may be arranged so that the inlet valve 18 is on the lower side and the discharge valve 20 on the upper side of the cylinder. The provision of the transducer 56, which has a sensing surface 57, and forms an end closure of the chamber 84, is also advantageous. Not shown is a passage entering the chamber 84 through which a temperature probe may be disposed for sensing the temperature of the fluid in the chamber during operation of the system 10.

The operation of the system 10, including the apparatus 14, to make suitable vapor pressure measurements in accordance with an improved method of the present invention will now be described in conjunction with the schematic diagram of FIG. 3A and 3B. The graphic depictions of pressure versus time and piston position versus time are intended to be read together, and further in company with the schematic showing of the positions of the piston 82 with respect to the chamber 84, in the interest of clarity.

Referring briefly, however, to FIG. 1, in operation the system 10 is, for example, typically used for measuring the vapor pressure of a liquid being pumped through a pipeline such as a crude oil flowstream blended with natural gasoline liquids (NGL). Accordingly, the conduits 22 and 34 are illustrated as being connected to a pipeline 120 wherein liquid is withdrawn from the pipeline through the conduit 22 and the pressure is increased to that sufficient to overcome pressure losses in the system 10 and to reinject the liquid into the pipeline through the conduit 34. In operation, the liquid is passed through the heating apparatus 28 to bring the temperature to that approximately equal to pipeline temperature, or to any selected temperature, including that necessary to comply with standard test conditions, and then pumped through the conduit 32 and the apparatus 14 or the conduit 46. If the apparatus 14 is in the process of making a vapor pressure measurement, the valves 18 and 20 are closed and the fluid not being sampled is bypassed through the conduit 46 to the conduit 34. When the valves 18 and 20 are opened, flow is diverted substantially through the cylinder chamber 84 to inject a new sample for testing and to remove the sample previously tested.

As will be appreciated from the foregoing description, the variables which are monitored to determine vapor pressure include reading the signals output from the displacement transducer 94 to determine the volume of the chamber 84, measuring the pressure sensed by the pressure transducer 56, and measuring the temperature of the liquid being conducted to or in the apparatus 14 using the temperature sensors 58, 60 or the aforementioned sensor which may be used to measure temperature in the chamber 84.

Figure 3A:
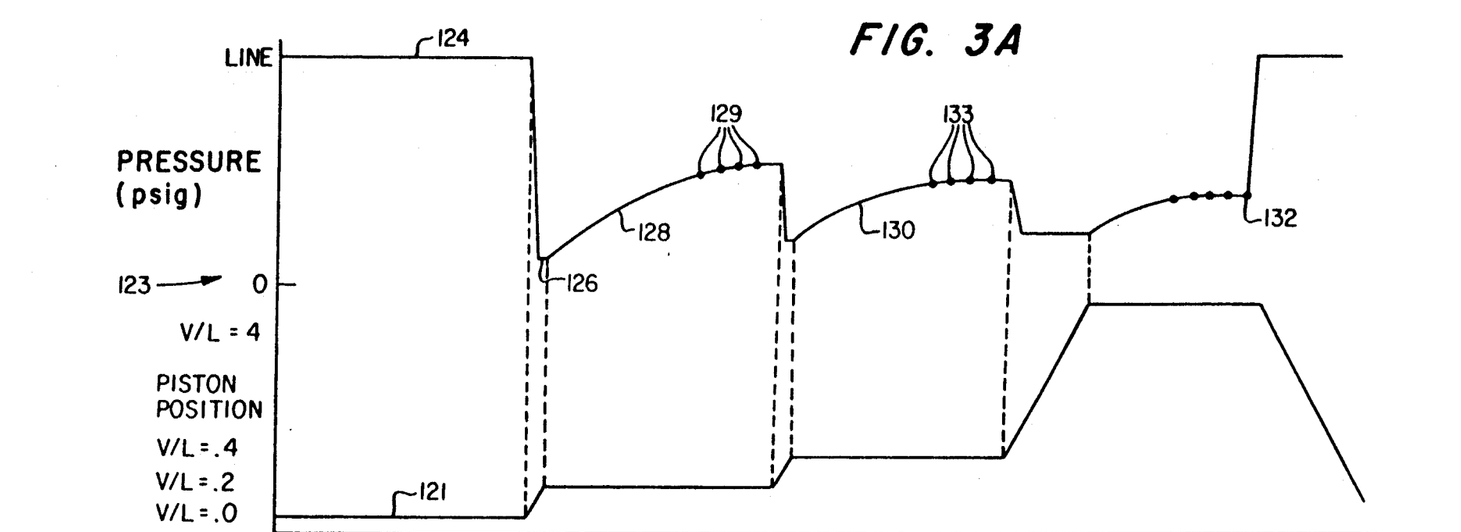
FIG. 3A and FIG. 3B comprise a schematic diagram showing the measured pressures and piston position with respect to time for the measurement apparatus.
Figure 3B:
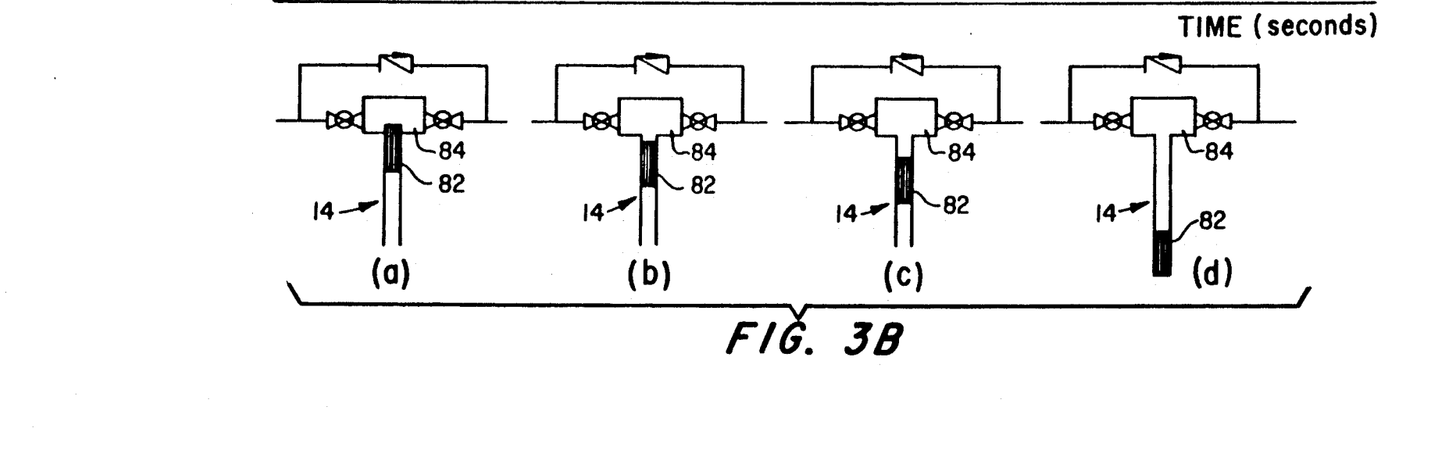

Referring to FIG. 3A and FIG. 3B, there is illustrated the sequence of events that occur to actually measure the true vapor pressure of a liquid sample trapped in the chamber 84. Reading the schematic diagrams of the apparatus 14 from left to right in FIG. 3B, the diagram (a) illustrates the condition wherein the valves 18 and 20 are open and flow of the process liquid is through the chamber 84 toward obtaining a new sample. Diagram (b) shows the valves 18 and 20 closed and fluid bypassing the chamber 84 through the conduit 46 and the check valve 48. In this condition of the apparatus 14, the piston 82 has moved to a first chamber expansion condition, which is preferably referenced as an incremental increase in the volume of the chamber 84, designated "V", which is the volume available for vapor, with respect to the initial volume of the chamber 84 when it is completely filled with liquid in the condition of diagram (a), which volume is designated "L". The total volume of chamber 84 in diagrams (b), (c) and (d) would be V plus L.

In the condition of the apparatus 14 according to the diagram (b), the ratio V/L is 0.2. After pressure and temperature measurements are taken at this condition over a defined period of time, the piston 82 is further stroked by the actuator 16 until the chamber volume is changed to a condition indicated by diagram (c) wherein $V/L = 0.4$. Measurements are again taken of pressure and temperature in the chamber 84 at this condition over a defined period of time. Finally, the piston 82 is stroked to the position indicated by the diagram (d) which corresponds to a chamber volume change to $V/L = 4.0$. At least one pressure measurement is taken after a predetermined period of time in this condition and appropriately recorded using the method of the present invention. After all measurements are taken, the valves 18 and 20 are reopened and the piston 82 is stroked back to the position indicated by the diagram (a) whereupon a new operating cycle may begin with a new sample of liquid.

At each volume condition of the chamber 84 according to diagrams (b) and (c), the pressure in the chamber is sampled over a period of time ranging from 30 to 300 seconds, depending on the type of fluid being tested. Typically, in measuring a sample of crude oil, pressure values are measured and recorded at intervals of one second over the last thirty to one hundred fifty seconds of the measurement interval. Referring further to FIG. 3A and, particularly, the diagram 123 of pressure in the chamber 84 versus time, the line 124 indicates the pressure in the chamber when the valves 18 and 20 are open and a new sample is being flowed through the chamber. Upon closure of the valves 18 and 20 and stroking of the piston 82, indicated generally by line 121, to a chamber volume corresponding to $V/L = 0.2$, the pressure in chamber 84 decreases initially to the value indicated by the short horizontal line 126. Over the first measurement time period, indicated by the abscissa of the diagram 123, the pressure in the chamber 84 will rise along the line 128 toward an equilibrium vapor pressure. Although an equilibrium vapor pressure will not be reached in a matter of a few seconds, in a process control type application of the system 10, long periods of measurement cannot be tolerated. Accordingly, in an effort to shorten the measurement period, the pressure versus time curves 128 and 130 shown at the various ratios of V/L, are modelled using an exponential function. The pressure values taken during the last thirty to one hundred fifty seconds of a particular expansion, such as measurements taken at points 129 and 133, for example, are fitted to the function:

$$P = \exp(a + b/\sqrt{t})$$

where P is pressure, exp is the natural logarithm "e", a and b are constants determined from a least squares analysis, and t is time. The determination of the constants a and b may be obtained from the approximate solution of a set of simultaneous equations of the first degree when the number of equations is greater than the number of unknowns (least squares method) which is described in Mark's Standard Handbook For Mechanical Engineers, 8th Edition, McGraw-Hill Book Company, New York, N.Y. As time t goes to infinity, the pressure P approaches an asymptotic value:

$$P_{asym} = \exp(a)$$

This asymptotic pressure $P_{V/L1}$ and $P_{V/L2}$ is calculated for the first two expansions of $V/L1 = 0.2$ and $V/L2 = 0.4$ and then extrapolated back to the condition of $V/L = 0$ to determine so-called true vapor pressure (TVP) using a straight-line approximation wherein:

$$TVP = P_{V/L1} - V/L1(P_{V/L1} - P_{V/L2})/(V/L1 - V/L2)$$

The resulting calculated true vapor pressure (TVP) very slightly underestimates the actual true vapor pressure. The exact underestimation will depend to some extent on the fluid being tested.

The final expansion to $V/L = 4.0$ is not extrapolated to infinite time. The pressure measured under this condition is of a two-phase mixture that has been approaching equilibrium from anywhere from 90 seconds to 15 minutes, depending on the time settings of the measurement intervals of the system 10. Experience has indicated that at the end of this time period the pressure is not changing noticeably, so the measured absolute pressure at point 132, for example, is recorded. Emergency standards delineated by the American Society of Testing Materials (ASTM) use the equivalent "absolute" pressure to compute what is called a dry vapor pressure equivalent.

Although a preferred embodiment of a vapor pressure measurement apparatus and method have been described hereinabove, those skilled in the art will recognize that various substitutions and modifications may be made to the invention without departing from the scope and spirit of the recitation in the appended claims.

What is claimed is:

1. An apparatus for measuring the vapor pressure of a liquid composition comprising:
   means forming a cylinder defining a closable expansible chamber for holding a liquid sample, said cylinder being mounted to receive liquid for taking sample measurements in such a way that the longitudinal central axis of said chamber is substantially horizontal so as to minimize the depth of liquid in said cylinder during expansion of said chamber;
   piston means disposed in said cylinder for reciprocating movement to change the volume of said chamber from a first minimum volume to larger volumes;
   pressure-sensing means exposed to said chamber for sensing the pressure in said chamber in response to a change in volume of said chamber;
   means for maintaining said liquid sample at a substantially constant, predetermined temperature in said chamber; and
   means for moving said piston with respect to said cylinder to a selected set of volumes of said chamber, respectively.

2. The apparatus set forth in claim 1, including:
   pump means in communication with a source of liquid to be sampled for conducting liquid through said means for maintaining said temperature; and
   bypass conduit means for conducting liquid around said cylinder during a sample measurement to maintain a flowstream of liquid through said apparatus.

3. The apparatus set forth in claim 1 wherein:
   the ratio of the diameter of said piston to the maximum stroke of said piston during measurements of said vapor pressure is less than 1.0.

4. The apparatus set forth in claim 1 wherein:
   said pressure-sensing means comprises a closure member for one end of said cylinder and defining an end wall of said chamber.

5. The apparatus set forth in claim 1 wherein:
   said cylinder includes inlet and outlet valve means for conducting liquid to said chamber and from said chamber, respectively, said valve means comprising closable ball valves having closure members disposed in proximity to said chamber so as to minimize available space between said closure members and said chamber for trapping vapor bubbles during a measurement process.

6. An apparatus for measuring the vapor pressure of a liquid composition comprising:
   means forming a cylinder defining a closable chamber for holding a liquid sample;
   piston means disposed in said cylinder for movement to change the volume of said chamber from a first minimum volume to larger volumes;
   pressure-sensing means exposed to said chamber for sensing the pressure in said chamber in response to a change in volume of said chamber, said pressure-sensing means comprising a closure member for one end of said cylinder and defining a transverse end wall of said chamber; and
   means for moving said piston with respect to said cylinder to a selected set of volumes of said chamber.

7. The apparatus set forth in claim 6 wherein:
   the ratio of the diameter of said piston to the maximum stroke of said piston during measurements of said vapor pressure is less than 1.0.

8. The apparatus set forth in claim 6 including:
   means for sensing the temperature of said liquid sample in said chamber.

9. A method for making vapor pressure measurements of a liquid composition comprising the steps of:
   providing apparatus comprising a cylinder having a bore, piston means disposed in said bore for movement to expand a chamber formed at least in part by said bore and said piston means, and pressure-sensing means for measuring the pressure in said chamber;
   introducing a sample of liquid into said chamber and moving said piston means from a first position to a second position to effect a first expansion of the volume of said chamber;
   measuring the pressure in said chamber over a finite period of time while maintaining the volume of said chamber at said first expansion to obtain plural values of the pressure in said chamber; and calculating a resultant vapor pressure of a liquid sample in said chamber based on plural values of pressure measured while the volume of said chamber is maintained substantially constant at said first expansion of said chamber.

10. The method set forth in claim 9, including the step of:
moving said piston to a third position to provide a second expansion of the volume of said chamber to a volume greater than said first expansion;
making plural measurements of pressure in said chamber after said second expansion over a finite period of time and while the volume of said chamber is maintained substantially constant at said second expansion; and
calculating a resultant vapor pressure of said liquid sample based on plural values of pressure measured after said second expansion.

11. A method for making vapor pressure measurements of a liquid composition comprising the steps of:
providing apparatus comprising a cylinder having a bore, piston means disposed in said bore for movement to expand a chamber formed at least in part by said bore and said piston means, and pressure-sensing means for measuring the pressure in said chamber;
introducing a sample of liquid into said chamber and moving said piston means from a first position to a second position to effect a first expansion of the volume of said chamber;
measuring the pressure in said chamber over a finite period of time to obtain plural values of the pressure in said chamber; and
calculating a resultant vapor pressure of a liquid sample in said chamber based on plural values of pressure measured after said first expansion of said chamber wherein the resultant vapor pressure (P) is determined from the equation:
$P = \exp(a + b/\sqrt{t})$ where exp is the natural logarithm "e", a and b are constants and t is time of the measurement of pressure in the chamber.

12. The method set forth in claim 11 wherein:
said resultant values of pressure in said chamber are determined by an approximate solution of a set of simultaneous equations of the first degree when the number of equations is greater than the number of unknowns to determine the constants a and b.

13. The method set forth in claim 12, including the step of:
extrapolating the true vapor pressure of said liquid sample based on the resultant values of vapor pressure determined at said first expansion and said second expansion by a straight line approximation for a quantity of $V/L = 0$, wherein V is the incremental increase in volume of the chamber from an initial volume (L) of liquid composition in said chamber.

14. The method set forth in claim 13 wherein:
said straight-line approximation is carried out using the equation:

$TVP = P_{V/L1} - V/L1(P_{V/L1} - P_{V/L2})/(V/L1 - V/L2)$ where TVP is true vapor pressure, $P_{V/L1}$ and $P_{V/L2}$ are the resultant pressures in said chamber after said first expansion and said second expansion, respectively, and V/L1 and V/L2 are the ratios of the volume increase in said chamber from said first expansion to the initial volume of said chamber and from said second expansion to the initial volume of said chamber, respectively.

15. The method set forth in claim 14, including the step of:
moving said piston to a fourth position to expand the volume of said chamber to a third expansion volume greater than said second expansion and making at least one pressure measurement of the fluid pressure in said chamber; and
comparing the resultant values of pressure in said chamber after said first expansion and said second expansion with the pressure measured after said third expansion to determine the vapor pressure of said liquid.

16. An apparatus for measuring the vapor pressure of a liquid composition comprising:
means forming a cylinder defining a closable chamber for holding a liquid sample;
piston means disposed in said cylinder for reciprocating movement to change the volume of said chamber from a first minimum volume to larger volumes, said piston means including rod means extending from one end of said cylinder and of a diameter less than the diameter of said piston means to form an annular space between a bore wall of said cylinder and said rod means;
conduit means in communication with said cylinder for conducting liquid from said space to minimize leakage of liquid from said apparatus during a measurement process;
means for sensing a predetermined leakage rate in said conduit means;
pressure-sensing means exposed to said chamber for sensing the pressure in said chamber in response to a change in volume of said chamber;
means for maintaining said liquid sample at a substantially constant, predetermined temperature in said chamber; and
means for moving said piston means with respect to said cylinder to a selected set of volumes of said chamber, respectively.

17. A method for making vapor pressure measurements of a liquid composition comprising the steps of:
providing apparatus comprising a cylinder having a bore, piston means disposed in said bore for movement to expand a chamber formed at least in part by said bore and said piston means, and pressure-sensing means for measuring the pressure in said chamber;
introducing a sample of liquid into said chamber and moving said piston means from a first position to a second position to effect a first expansion of the volume of said chamber;
measuring the pressure in said chamber over a finite period of time to obtain plural values of the pressure in said chamber;
calculating a resultant vapor pressure of a liquid sample in said chamber based on plural values of pressure measured after said first expansion of said chamber;
moving said piston means to a third position to provide a second expansion of the volume of said chamber;
making plural measurements of pressure in said chamber after said second expansion over a finite period of time;

calculating a resultant vapor pressure of said liquid sample based on plural values of pressure measured after said second expansion and wherein the resultant vapor pressure (P) is determined after at least one of said expansions from the equation:

$P = \exp(a + b\sqrt{E})$ where exp is the natural logarithm "e", a and b are constants and t is time of the measurement of pressure in the chamber.

18. An apparatus for measuring the vapor pressure of a liquid composition comprising:

means forming a cylinder defining a closable and expansible chamber for holding a liquid sample and mounted to receive liquid for taking sample measurements in such a way that the longitudinal central axis of said chamber is substantially horizontal so as to minimize the depth of liquid in said cylinder during expansion of said chamber;

piston means disposed in said cylinder for movement to change the volume of said chamber from a first minimum volume to larger volumes;

pressure-sensing means exposed to said chamber for sensing the pressure in said chamber in response to a change in volume of said chamber, said pressure-sensing means comprising a closure member for one end of said cylinder and defining a transverse end wall of said chamber; and means for moving said piston with respect to said cylinder to a selected set of volumes of said chamber.

* * * * *

UNITED STATES PATENT AND TRADEMARK OFFICE
CERTIFICATE OF CORRECTION

PATENT NO. : 5,172,586
DATED : December 22, 1992
INVENTOR(S) : Donald B. Reed

It is certified that error appears in the above-identified patent and that said Letters Patent is hereby corrected as shown below:

Column 9, line 39, delete "$P=\exp(a + b/\sqrt{E})$" and insert --- $P=\exp(a + b/\sqrt{t})$ ---.

Column 11, line 6, delete "$P=\exp(a + b/\sqrt{E})$" and insert --- $P=\exp(a + b/\sqrt{t})$ ---.

Signed and Sealed this

Twenty-sixth Day of October, 1993

Attest:

BRUCE LEHMAN

Attesting Officer

Commissioner of Patents and Trademarks